United States Patent
Macknik et al.

(10) Patent No.: US 11,707,193 B2
(45) Date of Patent: *Jul. 25, 2023

(54) SYSTEMS AND METHODS FOR USING EYE MOVEMENTS TO DETERMINE TRAUMATIC BRAIN INJURY

(71) Applicant: DIGNITY HEALTH, San Francisco, CA (US)

(72) Inventors: Stephen L. Macknik, Anthem, AZ (US); Susana Martinez-Conde, Anthem, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 17/063,473

(22) Filed: Oct. 5, 2020

(65) Prior Publication Data

US 2021/0015361 A1 Jan. 21, 2021

Related U.S. Application Data

(63) Continuation of application No. 16/264,131, filed on Jan. 31, 2019, now Pat. No. 10,791,926, which is a
(Continued)

(51) Int. Cl.
*A61B 3/113* (2006.01)
*A61B 5/00* (2006.01)
*A61B 5/11* (2006.01)

(52) U.S. Cl.
CPC ............ *A61B 3/113* (2013.01); *A61B 5/1103* (2013.01); *A61B 5/4064* (2013.01); *A61B 5/746* (2013.01); *A61B 5/74* (2013.01)

(58) Field of Classification Search
CPC ..... A61B 3/113; A61B 5/1103; A61B 5/4064; A61B 5/746; A61B 5/74
(Continued)

(56) References Cited

U.S. PATENT DOCUMENTS 4,815,839 A 3/1989 Waldorf
5,137,345 A 8/1992 Waldorf et al.
(Continued)

FOREIGN PATENT DOCUMENTS

CA 2857924 A1 1/2016
WO 2013078461 A1 5/2013
(Continued)

OTHER PUBLICATIONS

Hafed, et al., Microsaccades as an Overt Measure of Covert Attention Shifts, Vision Research, 2002, 42:2533-2545.
(Continued)

*Primary Examiner* — Mohammed A Hasan
(74) *Attorney, Agent, or Firm* — Quarles & Brady LLP

(57) ABSTRACT

Systems and methods for detecting a traumatic brain injury (TBI). The system comprises a sensing arrangement and a control unit. The sensing arrangement collects eye movement data of a user. The control unit is in communication with the sensing arrangement and configured to compare the eye movement data to one or more baseline measurements of eye movement dynamics. The control unit is also configured to generate an alert indicating the presence or severity of the TBI for delivery to control unit administrator if the eye movement data diverges from one or more of the baseline measurements by a threshold amount.

20 Claims, 2 Drawing Sheets

Related U.S. Application Data continuation of application No. 15/504,166, filed as application No. PCT/US2015/046117 on Aug. 20, 2015, now Pat. No. 10,231,617.

(60) Provisional application No. 62/040,166, filed on Aug. 21, 2014.

(58) Field of Classification Search
USPC .......................................................... 351/209
See application file for complete search history.

(56) References Cited

U.S. PATENT DOCUMENTS

| | | |
|---|---|---|
| 5,360,971 A | 11/1994 | Kaufman et al. |
| 5,382,989 A | 1/1995 | Uomor et al. |
| 8,348,428 B2 | 1/2013 | Martinez-Conde et al. |
| 8,668,337 B2 | 3/2014 | Waldorf et al. |
| 8,721,081 B2 | 5/2014 | Martinez-Conde et al. |
| 8,808,179 B1 | 8/2014 | Cinberg |
| 9,101,312 B2 | 8/2015 | Waldorf et al. |
| 9,301,679 B2 | 4/2016 | Martinez-Conde et al. |
| 10,231,166 B2 | 3/2019 | Li et al. |
| 10,231,617 B2 | 3/2019 | Macknik et al. |
| 11,013,441 B2 | 5/2021 | Samadani |
| 2003/0028081 A1 | 2/2003 | Blazey et al. |
| 2007/0013868 A1 | 1/2007 | Pugach et al. |
| 2009/0198148 A1 | 8/2009 | Lonky |
| 2009/0232357 A1 | 9/2009 | Angell et al. |
| 2010/0094161 A1 | 4/2010 | Kiderman et al. |
| 2010/0191156 A1 | 7/2010 | Sakamoto et al. |
| 2010/0277693 A1 | 11/2010 | Martinez-Conde et al. |
| 2013/0184781 A1 | 7/2013 | Eskandar et al. |
| 2013/0336547 A1* | 12/2013 | Komogortsev ........ A61B 5/163 382/117 |
| 2014/0114165 A1 | 4/2014 | Walker et al. |
| 2014/0330335 A1* | 11/2014 | Errico .................. A61B 5/6898 607/45 |
| 2015/0313496 A1* | 11/2015 | Connor .................. A61B 5/369 600/301 |
| 2016/0007849 A1* | 1/2016 | Krueger ................... A61B 5/11 600/301 |
| 2016/0022137 A1 | 1/2016 | Wetzel et al. |
| 2016/0262608 A1* | 9/2016 | Krueger ................ G16H 40/63 |
| 2017/0131766 A1 | 5/2017 | He et al. |
| 2017/0135577 A1* | 5/2017 | Komogortsev ........ A61B 5/168 |
| 2018/0008142 A1* | 1/2018 | Garoon ................ A61B 3/0025 |
| 2019/0200862 A1* | 7/2019 | Krueger ................ A61B 3/112 |

FOREIGN PATENT DOCUMENTS

| | | | | |
|---|---|---|---|---|
| WO | WO-2013078461 A1 * | 5/2013 | ............. | A61B 3/113 |
| WO | 2015051272 A1 | 4/2015 | | |
| WO | 2015167992 A1 | 11/2015 | | |

OTHER PUBLICATIONS

PCT International Search Report and Written Opinion, PCT/US2015/046117, dated Nov. 19, 2015, 11 pages.

European Patent Office, Extended European Search Report, Application No. 15833830.1, dated Apr. 18, 2018, 9 pages.

Office Action for Canada Patent Application No. 2,995,803, dated Oct. 5, 2021 (5 pages).

* cited by examiner

SYSTEMS AND METHODS FOR USING EYE MOVEMENTS TO DETERMINE TRAUMATIC BRAIN INJURY

CROSS-REFERENCE TO RELATED APPLICATIONS

This application is a continuation of U.S. patent application Ser. No. 16/264,131, filed Jan. 31, 2019, which is a continuation of U.S. patent application Ser. No. 15/504,166, filed Feb. 15, 2017, now U.S. Pat. No. 10,231,617, which represents the U.S. National Stage of International Application No. PCT/US2015/046117, filed Aug. 20, 2015, which is based on and claims the benefit of U.S. Provisional Patent Application Ser. No. 62/040,166, filed on Aug. 21, 2014, the contents of which are incorporated herein by reference in their entirety.

STATEMENT REGARDING FEDERALLY SPONSORED RESEARCH

N/A

BACKGROUND OF THE INVENTION

The present disclosure generally relates to systems and methods for acquiring data from a subject and, more particularly, to systems and methods for gathering and analyzing information about the subject's eye movements to determine or predict a state of the subject, including conditions such as traumatic brain injury (TBI) and other neurological injuries and diseases.

Brain injury can affect motor and cognitive function in the injured subject, and may increase the subject's vulnerability to a subsequent brain injury. When the brain injury is caused by trauma, such as an impact or piercing of the head, the subject is many times more likely to suffer a more severe injury the next time a similar trauma occurs. Concussion and other TBIs are currently at the forefront of sports medicine discussions, particularly for contact sports, because the risk to players is significant and the presence of a TBI cannot always be quickly diagnosed. For example, American football players are constantly at risk of a concussion, but often return to the game after a TBI because their visible symptoms were not cause for concern and a quick objective test is not available.

Another problem with diagnosing TBI is that most symptoms can be transient. Thus, with the passage of time it becomes more difficult to detect an injury, and medical examinations and accident investigations can be compromised. Early, quick, and objective detection of the physiological effects of TBI is needed.

The eye movements of people with neurological disease differ significantly from those of healthy people. The eyes in both populations do not stay perfectly still during visual fixation. Fixational eye movements and saccadic intrusions continuously change the position of the gaze. Microsaccades are rapid, small-magnitude involuntary saccades that occur several times each second during fixation; microsaccades counteract visual fading and generate strong neural transients in the early visual system. Microsaccades may also drive perceptual flips in binocular rivalry. Microsaccade rates and directions are moreover modulated by attention, and thus generate rich spatio-temporal dynamics. Further, fixational eye movements as a whole enhance fine spatial acuity. Abnormalities and intrusions in these eye movements can belie neurological impairments.

It would be beneficial to be able to detect TBI and differentially diagnose it from another neurological injury or disease in a non-invasive manner. The following disclosure provides one such differential diagnostic method.

SUMMARY OF THE INVENTION

The present invention overcomes drawbacks of previous technologies by providing systems and methods that afford a number of advantages and capabilities not contemplated by, recognized in, or possible in traditional system or known methodologies related to tracking or determining a subject's state, including the detection of traumatic brain injury (TBI) and other neurological injuries and diseases.

In one embodiment of the present invention, systems and methods are provided for monitoring, recording, and/or analyzing eye movements in situ to determine whether oculomotor dynamics are being affected by the onset or presence of TBI. Eye saccades and the velocity of intersaccadic eye drift are detectably affected by the onset or presence of these conditions. A system and method may alert a user to the presence of these states or conditions in a testing environment. In particular, a system in accordance with the present invention may include devices and device assemblies that record baseline data of a subject and generate a data model representing the eye movement data of the subject, and further the system may include device and device assemblies that record eye movement data in situ and compare it to the data model to determine if the user is affected by TBI. In one aspect, a sensor arrangement may include a camera and recording assembly for detecting and recording the eye movements.

In a contemplated embodiment of the present invention, a system includes a sensing arrangement that collects eye movement data of a user, and a control unit in communication with the sensing arrangement. The control unit may be configured to compare the eye movement data to one or more baseline measurements of eye movement dynamics and, if the eye movement data diverges from one or more of the baseline measurements by a threshold amount, generate an alert indicating the presence or severity of a TBI for delivery to the user. Comparing the eye movement data to the baseline measurements may include calculating a current intersaccadic drift velocity of the user and comparing the current intersaccadic drift velocity to one or more threshold drift velocities of the baseline measurements. The eye movement data may include one or more saccade parameters, and comparing the eye movement data to the baseline measurements may include calculating a current intersaccadic drift velocity of the user from the saccade parameters and comparing the current intersaccadic drift velocity to one or more threshold drift velocities of the baseline measurements.

In another embodiment of the present invention, a method of determining a TBI of a user includes recording from the user eye movement data of one or both of the user's eyes, comparing the eye movement data to one or more baseline measurements, and, if the eye movement data diverges from one or more of the baseline measurements by a threshold amount, delivering an alert indicating the presence or severity of a TBI to the user. The eye movement data may include one or both of saccade parameters and intersaccadic drift parameters.

In another embodiment of the present invention, systems and methods of the present invention may be combined as a kit or apparatus, whose advantages and capabilities will be readily apparent from descriptions below.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

DETAILED DESCRIPTION

The systems and methods for detecting onset, presence, and progression of particular states, including traumatic brain injury (TBI), through observation of eye movements described herein. TBI is shown by the inventors to affect oculomotor dynamics, including saccadic metrics and intersaccadic drift metrics, with increasing severity as the injury progresses. In particular, intersaccadic drift velocity increases as TBI develops and progresses, and select oculomotor dynamics can be tracked against a baseline to alert a subject before the effects of TBI impair the subject's ability to perform certain actions, such as operating a motor vehicle.

The systems and methods described herein are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, specific disclosure related to the detection of TBI is provided, although it will be appreciated that the systems and methods may be applied for detection of any neurological injury or disease and for any subject without undue experimentation.

Using the approach of the present invention, a detection system may record eye movement data from a user, compare the eye movement data to a data model comprising threshold eye movement data samples, and from the comparison make a determination whether or not the user's brain function is suffering from or is subject to impairment by TBI. The detection system may alert the user or another party to take corrective action if onset or presence of a dangerous impaired condition is detected.

Figure 1:
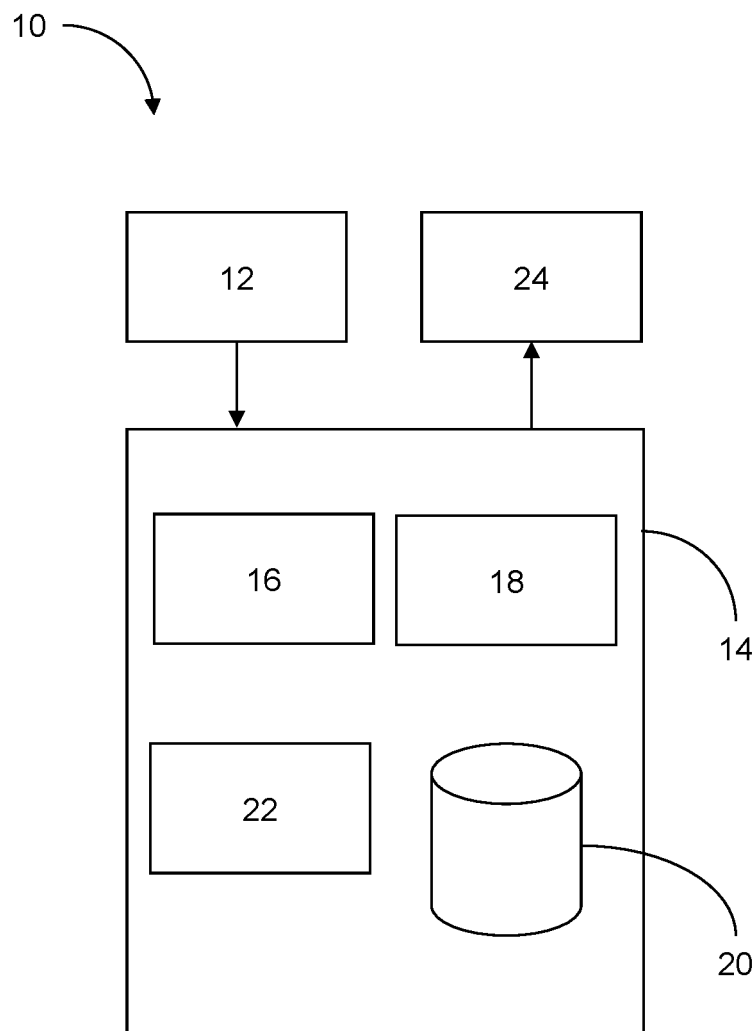
FIG. 1 is a diagram of a detection system in accordance with the present invention.

Referring to FIG. 1, an embodiment of the detection system 10 may include a sensing arrangement 12 configured to detect and record eye movement dynamics of the user. The sensing arrangement 12 may include one or more sensors suitable for collecting the eye movement data. Such sensors may include a camera or other imaging or motion tracking device capable of recording at a suitably high speed and level of detail so that the user's eye movement dynamics, including saccades and intersaccadic drift, are captured. A monocular arrangement of one or more sensors for one of the user's eyes may be used, or one or more sensors may be included for each eye to obtain binocular data. In some embodiments, the sensors may be miniaturized or otherwise compact, portable, and non-invasive. The sensors may further be vehicle-independent, and may be wireless, to facilitate integration of the sensors into any deployment of the detection system 10. For example, the sensing arrangement 12 may include sensors that are integrated into eyewear, such as on the frame or within the lenses of a pair of glasses. This allows for eye movement data collected even as the user turns his head, and allows the sensors to be positioned close to the eyes. In another example, the sensors may be integrated into a heads-up display for a vehicle. In another example, the sensors may be integrated into a handheld scanning device.

The sensing arrangement 12 may further include integrated or discrete devices for processing, storing, and transmitting collected data. Such devices may include a processor, volatile and/or permanent memory, a wired or wireless transmitter, and associated power circuits and power supply for operating the devices. Software modules may define and execute instructions for operating the sensors, configuring databases, registers, or other data stores, and controlling transmission of the data. The collected data may be shared via transmission to a control unit 14 that may be integrated with or disposed physically remotely from the sensing arrangement 12. The eye movement data, or a subset thereof, may be transmitted in real-time as it is captured by the sensors, or it may be stored for later transmission.

The control unit 14 may use the processing hardware (i.e., processor, memory, and the like) of the sensing arrangement 12, or may include its own processing hardware for analyzing the eye movement data and generating an alert to the user if needed. The control unit 14 may include a plurality of modules that cooperate to process the eye movement data in a particular fashion, such as according to the methods described below. Each module may include software (or firmware) that, when executed, configures the control unit 14 to perform a desired function. A data analysis module 16 may extract information from the eye movement data for comparison to the data model. The data analysis module 16 may include one or more data filters, such as a Butterworth or other suitable bandpass filter, that retain only desired signal elements of the eye movement data. The data analysis module 16 may include program instructions for calculating, from the eye movement data, one or more eye movement dynamics, such as saccades and/or intersaccadic drift velocities, of the user's eyes. The calculation may be performed substantially in real-time, such that a calculated intersaccadic drift velocity may be considered the current drift velocity of the user's eyes.

A comparison module 18 may receive the processed eye movement data from the data analysis module 16 and may compare it to the data model as described in detail below. The control unit 14 may include or have access to a model data store 20 that stores the data model. The model data store 20 may be a database, data record, register, or other suitable arrangement for storing data. In some embodiments, the data model may simply be a threshold drift velocity, and may thus be stored as a single data record in memory accessible by the comparison module 18. In other embodiments, the data model may be a lookup table, linked list, array, or other suitable data type depending on the data samples for eye movement dynamics needed to be stored in the data model.

In some embodiments, the control unit 14 may include a data model generator 22. The data model generator 22 is a module that receives eye movement data collected by the sensing arrangement 12 during a modeling step as described below. The data model generator 22 may extract, or cause the data analysis module 16 to extract, information from the collected eye movement data that will constitute the threshold eye movement data samples in the data model. The data model generator 22 may then create the data model from the threshold eye movement data samples, and may store the data model in the model data store 20. In other embodiments, the data model may be generated and stored in the model data store 20 by a separate modeling unit (not shown) of the system 10. The modeling unit may include its own sensing arrangement, processing hardware, and program modules. One suitable modeling unit may be the EyeLink 1000 by SR Research Ltd. of Mississauga, Ontario, Canada.

The control unit 14 may include or communicate with an alerting arrangement 24 configured to produce an alert to the user according to the results of the data comparison in the comparison module 18. The alerting arrangement may be any suitable indicator and associated hardware and software for driving the indicator. Suitable indicators include, without limitation: a visual display such as one or more light-emitting diodes, a liquid crystal display, a projector, and the like; a bell, buzzer, or other audible signaling means; and a piezoelectric or other vibrating device.

Figure 2:
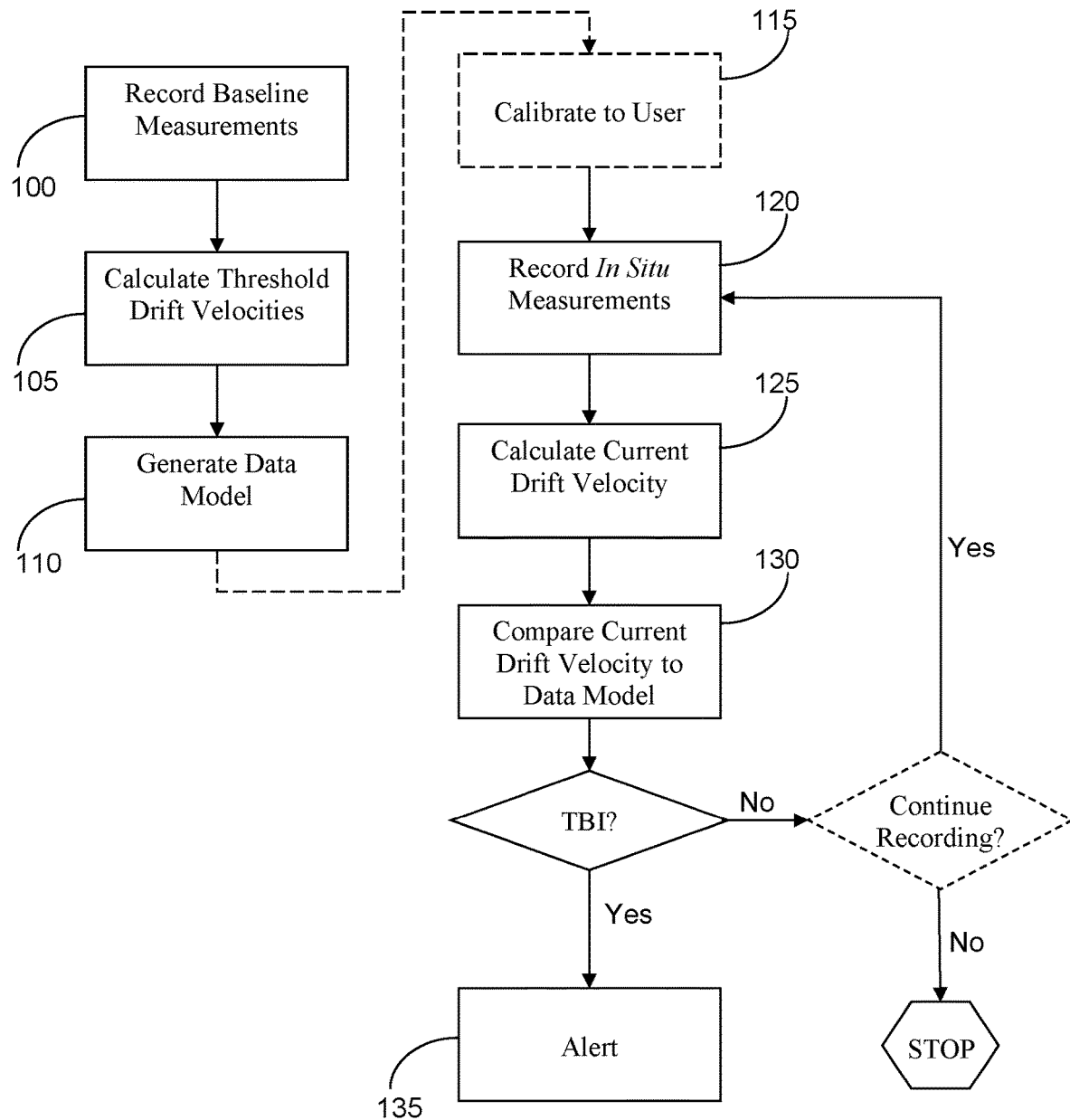
FIG. 2 is a flowchart illustrating a method for detecting traumatic brain injury in accordance with the present invention.

The detection system 10 may be used to execute any suitable method of detecting dangerous conditions that are indicated by eye movement data. Referring to FIG. 2, the detection system 10 may execute a method of detecting onset or presence of TBI in the user. At step 100, the system may record baseline measurements of the eye movement dynamics for the data model. The baseline measurements are taken of a subject which may or may not be the user. It may be advantageous that the data model use baseline measurements of the user himself in order to individualize the operation of the system, but the baseline measurements may be taken from a non-user subject, or taken from a plurality of subjects and averaged if desired. The conditions in which the baseline measurements are recorded may depend on the desired specificity of the data model. In some embodiments, the baseline measurements may be taken in normal conditions. In other embodiments, the baseline measurements may be taken in known injured conditions.

At step 105, the system may calculate one or more threshold drift velocities from the recorded baseline measurements. The threshold drift velocities may depend on the format of the collected baseline measurements. For example, where only normal-condition or only injured-condition baseline measurements were taken, a single threshold drift velocity (i.e., threshold-normal or threshold-TBI drift velocity) may be calculated. At step 110, the system may generate the data model for the baseline-tested subject(s). The data model may represent the progression of the intersaccadic drift velocity of the subject from normal conditions to injured conditions, and further beyond a TBI threshold into increasingly severe injury. The data model may be generated and stored in any suitable format that allows the system to subsequently compare eye movement data collected in situ from the user against the data model to determine the user's current impairment.

The steps 100, 105, 110 for obtaining the data model may be performed at any suitable time before testing the user in situ for signs of TBI. In one embodiment, the steps 100-110 may be performed far in advance and remotely from the test environment. In another embodiment, the steps 100-110 may be performed in the test environment, immediately preceding testing the user. For example, the user may activate the system 10, such as by donning and activating eyewear housing the sensing arrangement 12, which initiates step 100 of recording the baseline measurements in the present conditions. This may be in normal conditions, such as when the user is about to drive his vehicle in the morning, and only the normal eye movement data would be collected as baseline measurements. In still other embodiments, the data model may be created by the system 10 or another system using a different method than described above.

At step 115, optionally the system may calibrate itself to the user if the data model or comparison method require it. For example, the data model may be a standardized model generated from baseline measurements of (a) non-user subject(s), or the comparison method may determine the presence of TBI from a percentage deviation from the user's threshold-normal drift velocity value(s). See below. In such an embodiment, the system calibrates (step 115) by recording a calibration set, such as ten seconds or less but preferably five seconds or less, of eye movement data of the user when the system is activated in the test environment under normal conditions. The system may compare the calibration data to the data model. In one embodiment, this involves determining a deviation of the user's threshold-normal drift velocity from the threshold-normal drift velocity of the model. The system can then adapt the data model to the user.

At step 120, the system may record in situ eye movement data from the user continuously or at predetermined intervals while the system is activated. At step 125, the system may calculate, in real-time or at predetermined intervals, the user's current drift velocity. At step 130, the system may compare the current drift velocity to the data model to determine whether TBI has occurred. Such progression may be calculated within any suitable paradigm. Examples include, without limitation: ratio or percentage by which the current drift velocity exceeds the user's or the data model's threshold-normal drift velocity; ratio or percentage by which the current drift velocity is below or above the threshold-TBI drift velocity; comparison of current drift velocity to points on a curve between threshold-normal and threshold-TBI values in the data model; and the like. If the user is neither injured nor within a predetermined proximity to the threshold-TBI value of the data model, the system returns to step 120 and continues recording current data. In one configuration, the system can be optionally interrupted from continuing recording in situ measurements by an administrator or instructions installed in the control unit. Such instructions can be stopping recording when a predetermined duration has reached, the measurements are noisy or weak, or the administrator has entered a stop signal. If the user's condition warrants (i.e., the current drift velocity is above or within a certain range of the threshold-TBI value), at step 135 the system may alert the user to take corrective action.

In addition or alternatively to the methods described herein, the system may record and analyze eye movement data using any of the methods and system components described in copending U.S. patent application Ser. No. 14/220,265, co-owned by the present applicant and incorporated fully herein by reference.

The described system and methods may be implemented in any environment and during any task that may subject the user to dangerous conditions that affect eye movements. The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A method of determining a traumatic brain injury (TBI) of a user, the method comprising:
   a) obtaining eye movement data of one or both of the user's eyes;
   b) calculating, from the eye movement data, one or more current intersaccadic drift velocities;
   c) comparing the eye movement data, including the one or more current intersaccadic drift velocities, to a data model including intersaccadic drift velocities; and
   d) delivering an alert indicating results of the comparison, including one of a presence, absence, progression, or a severity of the TBI.

2. The method of claim 1, wherein the data model includes a threshold intersaccadic drift velocity.

3. The method of claim 1, wherein the data model includes a plurality of intersaccadic drift velocities plotted along a curve ranging at least between a threshold-normal value to a threshold-TBI value.

4. The method of claim 1, wherein the data model includes baseline measurements of eye movement dynamics.

5. The method of claim 4, wherein the baseline measurements of eye movement dynamics are derived from previous eye movement data of the user.

6. The method of claim 4, wherein the baseline measurements of eye movement dynamics are derived from eye movement data of a subject other than the user.

7. The method of claim 4, wherein the baseline measurements of eye movement dynamics are derived from averaged eye movement data of a plurality of subjects other than the user.

8. The method of claim 4, wherein the baseline measurements of eye movement dynamics are derived from eye movement data of one of the user or a subject other than the user taken in normal conditions without a TBI.

9. The method of claim 4, wherein the baseline measurements of eye movement dynamics are derived from eye movement data of one of the user or a subject other than the user taken in conditions with a diagnosed TBI.

10. The method of claim 1, wherein the data model represents a progression of eye movement dynamics of the user from a "normal" condition to an "injury" condition.

11. The method of claim 1 and further comprising calibrating the data model to the user prior to step c).

12. The method of claim 11, wherein calibrating the data model includes:
    obtaining a calibration set of eye movement data of one or both of the user's eyes;
    comparing the calibration set of eye movement data to the data model to determine a deviation of the calibration set of eye movement data from the data model; and
    adapting the data model to the user based on the comparison.

13. The method of claim 1, wherein delivering the alert includes providing a visual display of the results.

14. The method of claim 1, wherein step a) further includes recording the eye movement data from one or both of the user's eyes.

15. The method of claim 14 and further comprising continuing the recording until one of the alert indicates the presence of the TBI, a predetermined time duration has been reached, or a manual request to stop recording has been received.

16. The method of claim 1 and further comprising delivering a secondary alert to take corrective action when the results of the comparison indicate the eye movement data is one of above or within a certain range of a threshold-TBI value.

17. A system for determining or monitoring a traumatic brain injury (TBI) of a user, the system comprising:
    a sensing arrangement configured to capture eye movement data of the user;
    a control unit in communication with the sensing arrangement, the control unit being configured to:
        obtain the eye movement data from the sensing arrangement;
        calculate, from the eye movement data, one or more current intersaccadic drift velocities;
        compare the eye movement data, including the one or more current intersaccadic drift velocities, to a data model including intersaccadic drift velocities; and
        deliver an alert indicating results of the comparison, including one of a presence, absence, progression, or a severity of a TBI.

18. The system of claim 17, wherein the sensing arrangement is integrated into a handheld scanning device.

19. The system of claim 17, wherein the sensing arrangement is integrated into eyewear configured to be worn by the user.

20. The system of claim 17, wherein the control unit includes a data model generator configured to create the data model from prior eye movement data obtained from one of the user or one or more subjects other than the user.

* * * * *